United States Patent [19]

Lantz

[11] Patent Number: 4,934,200
[45] Date of Patent: Jun. 19, 1990

[54] SAMPLER FOR GRANULAR MATERIAL MOVING THROUGH A PIPE

[75] Inventor: Joel B. Lantz, Bedford Heights, Ohio

[73] Assignee: Neundorfer, Inc., Willoughby, Ohio

[21] Appl. No.: 293,291

[22] Filed: Jan. 4, 1989

[51] Int. Cl.$^5$ .............................................. G01N 1/08
[52] U.S. Cl. ................................................. 73/863.85
[58] Field of Search ........... 73/864.41, 864.45, 863.54, 73/863.71, 863.81, 863.82, 863.85, 836.86

[56] References Cited

U.S. PATENT DOCUMENTS

| | | | |
|---|---|---|---|
| 1,966,712 | 6/1930 | Fisher | 73/863.54 |
| 2,370,260 | 4/1943 | Robison | 73/863.54 |
| 3,158,030 | 10/1960 | Cross | 73/864.31 |
| 3,659,461 | 5/1972 | Thompson | 73/863.54 |
| 3,747,411 | 7/1973 | McDermott | 73/863.54 |
| 3,858,449 | 1/1975 | Singer | 73/863.86 X |
| 4,399,710 | 8/1983 | Schneider | 73/863.85 X |
| 4,433,587 | 2/1984 | Risdal | 73/863.54 |
| 4,562,747 | 1/1986 | Jaeger | 73/863.54 |

Primary Examiner—Hezron E. Williams
Assistant Examiner—Joseph W. Roskos
Attorney, Agent, or Firm—Michael Sand Co.

[57] ABSTRACT

A sampler for sampling granular material moving through a pipe includes a housing which is mounted on the pipe, and a probe having an open front end and a hollow rearwardly divergent interior movably mounted within the housing. A pair of pneumatic cylinders selectively move the probe between a retracted position within the housing and an extended position within the pipe. A pneumatic vibrator is mounted on the probe for selectively vibrating the probe providing for penetration of the granular material within the pipe and for moving samples of the material through the probe. Various resilient and abrasion resistant materials seal the probe to the housing, and a plurality of rollers are mounted within the housing for stabilizing and guiding the moving probe. A gate is movably mounted on a pneumatic cylinder for closing the open front end of the probe when the probe is in the retracted position. Following opening of the gate, the moving granular material in the pipe is penetrated by cutter tips formed on the front end of the probe, under the influence of the penumatic vibrator and the pneumatic cylinders within the housing. The captured sample moves toward the rear of the probe and out of a chute under the influence of the vibrator and gravity. The gate is closed after retraction of the probe from the pipe to prevent any further movement of sample from the pipe into the probe.

26 Claims, 5 Drawing Sheets

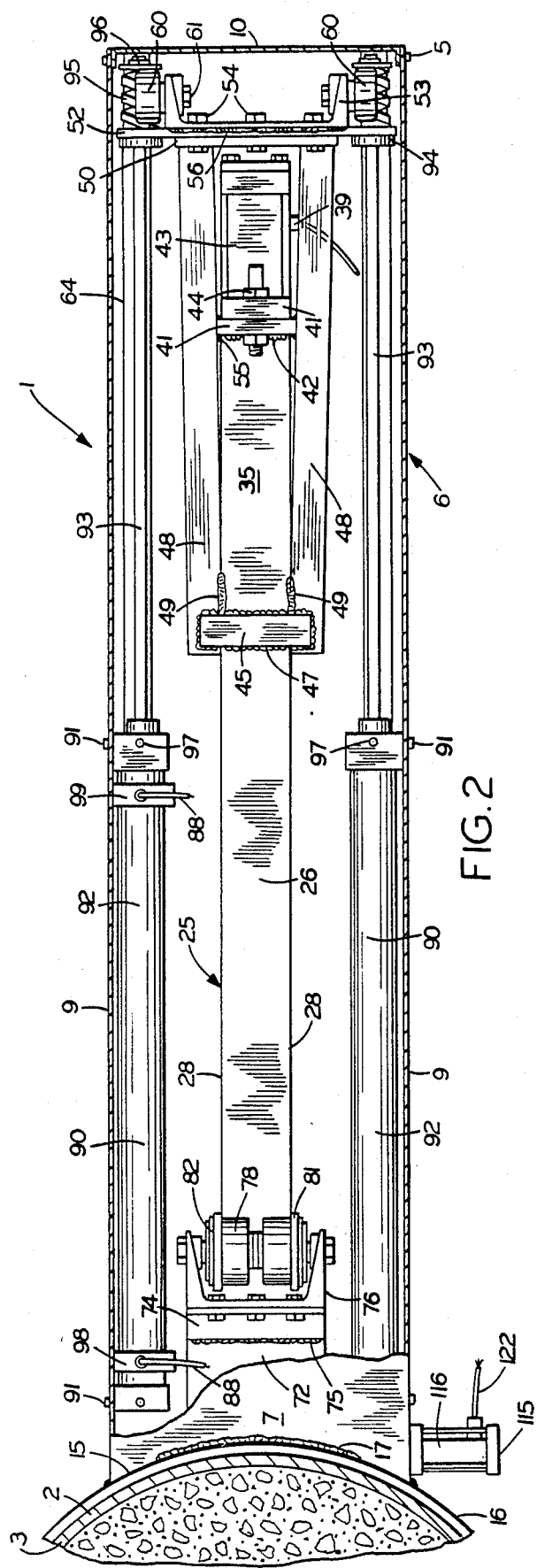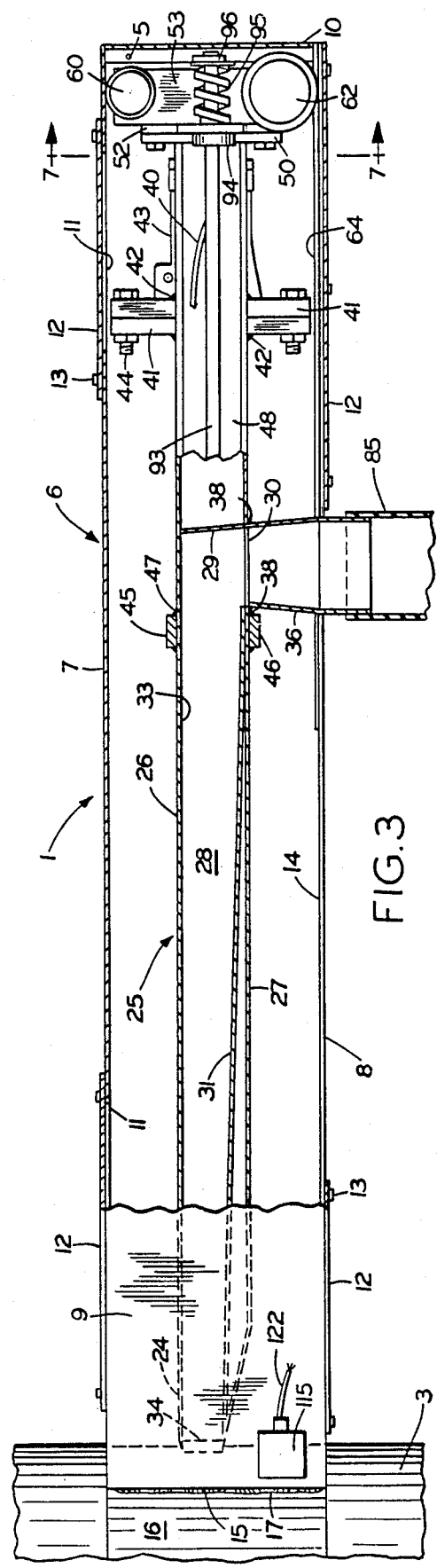

SAMPLER FOR GRANULAR MATERIAL MOVING THROUGH A PIPE

BACKGROUND OF THE INVENTION

1. Technical Field

The invention relates to sampling apparatus and in particular to a sampling apparatus for withdrawing a sample of non-free flowing granular material moving through a pipe. More particularly, the invention relates to such a sampling apparatus which withdraws samples of non-free flowing granular material moving through a pipe at a selected point along the pipe and at selected intervals, and which deposits the samples into a suitable receptacle.

2. Background Information

Various types of samplers have been used to withdraw samples of granular material or slurries from pipes or ducts. In many of these sampling apparatus, the material flows into an opening in a probe and is subsequently removed usually in one of three ways. Either the material pressure in the pipe forces the sample out of the probe, gravity causes the sample to move through and out of the probe, or a fixed increment of material is collected in a cavity at the end of the probe and is dumped into a chute such as by rotation of the cavity member. Such samplers depend on the flowability of the material into and/or out of the probe. Some examples of such prior art samplers are shown in U.S. Pat. Ser. Nos. 1,966,712, 2,370,260, 3,659,461, 3,747,411, and 4,433,587. However, several of the samplers shown and described in the above-listed patents are unsuitable for obtaining representative samples of non-free flowing materials, such as crushed coal or materials that have a tendency to plug up the probe opening. Also, many of these prior art sampling apparatus do not sample across the entire width of the pipe. Finally, all of these prior art samplers utilize a round tube which draws disproportionately larger amounts of sample material at the axis of the probe than the sides. This creates undesirable sample bias in a highly heterogeneous material such as coal.

Other types of known samplers utilize an auger to withdraw material out of a pipe. One example of such a sampler is the Model B Automatic Sampling System manufactured by Gustafson of Plano, Tex. While such samplers only require material to flow into the auger, the auger constantly remains in the pipe and creates a source of blockage for non-free flowing materials, especially when the material is wet. In addition, such routinely present protrusions are not permitted in coal pipes. Although retractable augers are utilized to extract coal samples vertically from truck and rail car beds, there is no known retractable auger adapted for use in pipes. Finally, these prior art auger-type samplers all utilize a round probe tube which, as discussed above when mounted on a pipe perpendicular to the movement of material within the pipe, takes disproportionately more sample at the axis of the probe than its sides.

A different principle has been applied in the known prior art to the sampling of coal from trucks and rail cars, in which both static and vibratory forces are applied vertically to a rectangular probe having a rigid cutting edge providing for filling of the probe with a core of the material to be sampled. Such a construction is shown and described in U.S. Pat. Ser. No. 3,158,030. In the sampler of this prior art patent, a pair of pneumatic closing gates hold the core sample in the probe following penetration of the material by the probe. The probe then is vertically withdrawn, moved horizontally to the location of discharge, and the gates opened to release the sample into a receptacle or onto a belt. This device does have the potential advantage of removing a long, uniform cross-section sample of a non-free flowing material. Also, the pneumatic vibrations greatly assist the penetration of the coal by the sampler probe and movement of material into the probe. However, although the general principle of static and vibratory penetration by a rectangular tube having a rigid cutting edge into a material is applicable in the present invention, known prior art samplers which utilize the vibratory theory require complete removal of the probe from the material being sampled and movement to another location for discharge of the sample, and the sample is discharged out of the same opening through which the sample entered the probe. In addition, there is no provision either to seal the vibrating rectangular probe into a pipe or to isolate such a pipe following removal of the probe.

It is known that the forces needed to move a solid material through a straight tube of narrow cross-section increase with the distance from the point of entry into the tube due to the increasing friction of cumulative layers of the material. Even with the assistance of vibratory forces, under certain conditions movement of such material into a straight three inch by three inch square probe, for example, rapidly becomes more difficult as the tube fills up. The rate of movement of material into the probe is critical for sampling from a non-free flowing material moving in a pipe, since as the length of time the probe remains inserted in the pipe increases, the chance of initiating blockages in the pipe also increases. This is especially critical where the material to be sampled has a high moisture content.

Thus, the need exists for an improved sampler for non-free flowing granular material moving through a pipe in which representative samples of the material can be quickly and efficiently removed from the pipe at a selected point along the pipe and at selected intervals without significantly blocking the pipe, and then deposited in a suitable receptacle for subsequent analysis.

SUMMARY OF THE INVENTION

Objectives of the invention include providing a sampler for granular material moving through a pipe in which a probe of the sampler is extensible into the pipe having a non-free flowing material moving therein, which quickly and efficiently withdraws a representative sample of the material without significantly blocking the material moving in the pipe, and which deposits the sample in a suitable receptacle for subsequent analysis.

Another objective of the invention is to provide such a sampler for granular material in which the sampler can withdraw material at virtually any selected point along the pipe at either regularly timed intervals or at other desired intervals, such as an interval based on a selected amount of material which has passed through the pipe.

Still another objective of the invention is to provide such a sampler in which material entering the probe has a tendency to loosen rather than packing with increasing filling of the probe to counteract the increasing frictional forces in the probe, and which promotes more rapid, uniform movement of material into and through the probe with relatively low penetration forces of the probe into the material to be sampled.

A further objective of the invention is to provide such a sampler in which vibratory forces are utilized to urge the probe into the material moving through the pipe rather than solely static forces.

A still further objective of the invention is to provide such a sampler in which the probe smoothly penetrates the granular material moving through the pipe.

Another objective of the present invention is to provide such a sampler in which, under normal conditions, the probe of the sampler does not fill with a core as in prior sampler apparatus, except near the open front end thereof, but rather as the sampled material loosens it flows through the probe and out of a slot or chute at the rear end of the probe by vibrational and gravitational transport.

A further objective of the invention is to provide such a sampler in which the probe can be quickly retracted out of the pipe to minimize attrition to the probe tip by the material stream, and in which the open front end of the probe can be closed to prevent further flow of material from the pipe into the probe between sample cycles.

Still another objective of the invention is to provide such a sampler which, when utilized for obtaining coal samples, obtains the coal samples within a few minutes of burning of the coal, without requiring shutting off the coal movement during the period of sampling and without requiring a very large sample to be taken.

A still further objective of the invention is to provide such a sampler in which the probe of the sampler extends across substantially the entire width of the pipe.

Another objective of the present invention is to provide such a sampler in which the probe is interfaced with the pipe without substantially dampening the vibratory forces imparted to the probe and impeding the vibratory movement of the probe.

A further objective of the invention is to provide such a sampler which is adapted to sample crushed coal especially in the electric power utility industry, minerals at processing plants, fly ash from electrostatic precipitators, and non-free flowing dry or moist food products.

Still another objective of the invention is to provide such a sampler which is relatively simple to maintain and operate, inexpensive, and durable in use.

These objectives and advantages are obtained by the improved apparatus of the invention for sampling a granular material moving through a pipe, the general nature of which may be stated as including, a housing having an open front end, the housing being mounted on the pipe so that the open front end is aligned with an opening formed in the pipe, a hollow probe having an open front end, the probe being movably mounted within the housing for removing a sample of the granular material from the pipe, means for selectively moving the probe between a retracted position within the housing and through the open front end of the housing to an extended position within the pipe, means for selectively vibrating the probe to assist the probe in penetrating the granular material within the pipe to obtain a sample of the granular material within the probe and for moving the sample through the probe, means for sealing the probe to the front end of the housing, and means for selectively closing the probe at a selected point along the probe to prevent movement of the granular material through the probe upon the probe moving toward a retracted position.

BRIEF DESCRIPTION OF THE DRAWINGS

Preferred embodiments of the invention, illustrative of the best modes in which applicant has contemplated applying the principles, are set forth in the following description and are shown in the drawings and are particularly and distinctly pointed out and set forth in the appended claims.

FIG. 2 is an enlarged fragmentary top plan view of the sampler as shown in FIG. 1, with portions broken away and in section;

FIG. 3 is an enlarged fragmentary side view of the sampler as shown in FIG. 1, with portions broken away and in section;

Similar numerals refer to similar parts throughout the drawings.

DESCRIPTION OF THE PREFERRED EMBODIMENT

Figure 1:
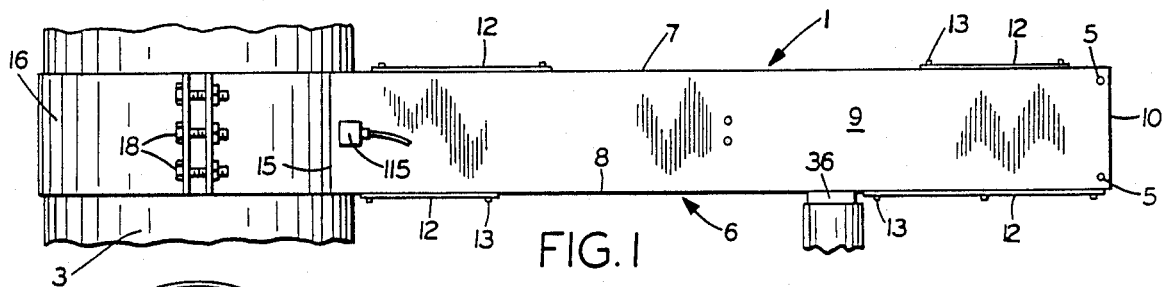
FIG. 1 is a fragmentary side elevational view of the improved sampler of the invention for sampling granular material moving through a pipe.

The improved apparatus of the present invention for sampling a granular material moving through a pipe is indicated generally at 1, and is shown particularly in FIGS. 1-3. Sampler 1 is especially useful for sampling crushed coal 2 as it moves through a pipe 3 from a bunker or silo into a feeder or mills, as is common in the electric power utility industry. However, sampling apparatus 1 also is useful in other applications such as for sampling minerals at processing plants, fly ash from electrostatic precipitators, and non-free flowing dry or moist food products.

Sampler 1 includes an elongated, rectangular-shaped housing indicated generally at 6, having top, bottom, side, and rear walls 7, 8, 9, and 10, respectively (FIGS. 1–3). Top, bottom and side walls 7, 8 and 9 of housing 6 preferably are formed as an integral one-piece member, and rear wall 10 is removably mounted on side walls 9 by usual fasteners 5 to provide access to the internal components of sampler 1 for maintenance, repair, etc. A plurality of openings 11 are formed in top and bottom walls 7 and 8 of housing 6 to provide additional access to the internal components of sampler 1. During normal operation of sampler 1, openings 11 are covered by plates 12 which are mounted on top and bottom walls 7 and 8 of housing 6 by fasteners 13. An elongated, longitudinally extending slot 14 (FIG. 3) is formed in bottom wall 8 of housing 6, the function of which will be described in greater detail below.

Figure 4:
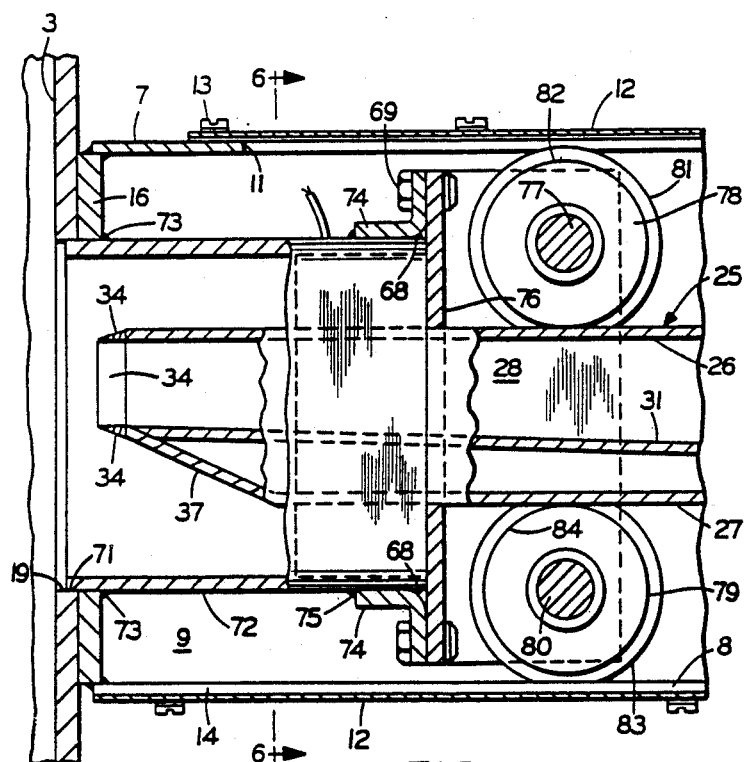
FIG. 4 is a greatly enlarged fragmentary side view of the front ends of the sampler housing and probe, with portions broken away and in section.

A front end 15 of housing 6 is substantially open and has a contour which is generally complementary to the contour of pipe 3 for snug mounting of the housing against the pipe (FIGS. 2 and 4). Open front end 15 of housing 6 is aligned with an opening 19 formed in pipe 3, and a circular clamp 16 which is attached to top, bottom and side walls 7, 8 and 9 of the housing by welds 17, is snugly tightened around the pipe by fasteners 18 to securely removably mount sampler 1 on the pipe. Housing 6 is formed of any suitable metal and preferably is press brake formed and punched.

Figures 7, 8:
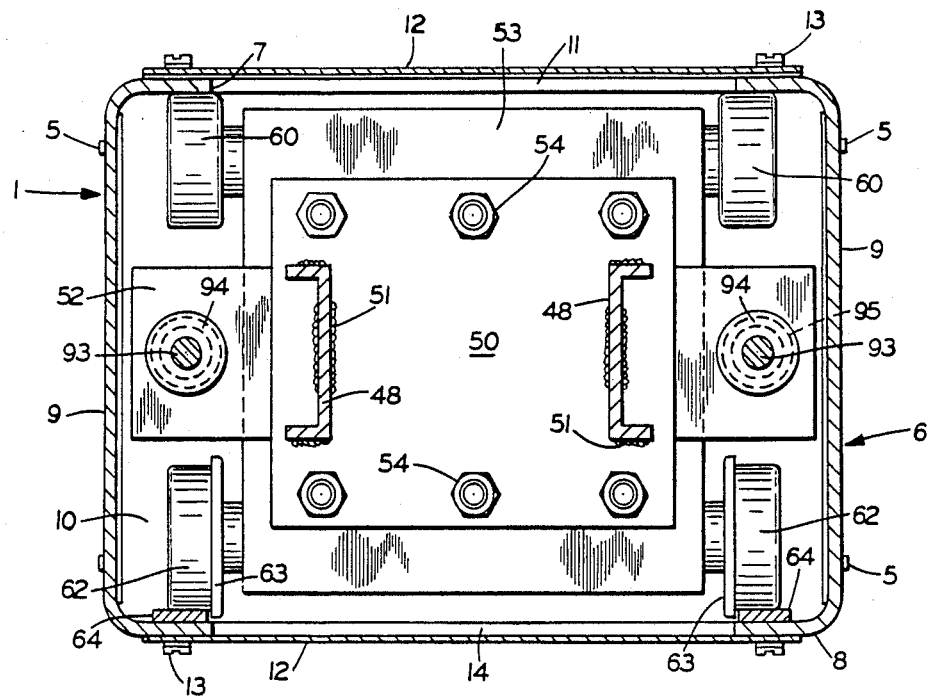
FIG. 7 is a greatly enlarged sectional view taken on line 7—7, FIG. 3.
FIG. 8 is a greatly enlarged fragmentary top view, with portions broken away and in section, of the gate for closing the open front end of the probe.

In accordance with one of the main features of the invention, an elongated, generally rectangular-shaped probe indicated generally at 25, for removing samples of coal 2 from pipe 3, is movably mounted within housing 6 (FIGS. 2 and 3). Probe 25 includes top, bottom, side and rear walls 26, 27, 28, and 29, respectively. A front end 24 of probe 25 includes an upwardly beveled portion 37 of bottom wall 27, and a beveled cutter tip 34 is formed on the front end of each of top, bottom and side walls 26–28 (FIGS. 4 and 8). Beveled portion 37 and cutter tips 34 provide for smooth penetration of coal 2 by probe 25. Probe 25 preferably is formed of stainless steel and cutter tips 34 are formed of any suitable material, such as 400-series stainless steel or a ceramic material.

A sample outlet opening 30 is formed in bottom wall 27 of probe 25 adjacent to rear wall 29 (FIG. 3). An interior wall 31 slopes downwardly rearwardly away from upwardly beveled portion 37 of bottom wall 27 and terminates adjacent to and frontwardly of outlet opening 30. Front end 24 of probe 25 is open, and top, side, rear, and interior walls 26, 28, 29, and 31 respectively, define a rearwardly divergent channel or hollow 33 within the probe through which samples of coal 2 can be withdrawn from pipe 3 as described below in the operation of sampling apparatus 1. A chute 36 is attached to bottom wall 27 of probe 25 by welds 38 and is aligned with outlet opening 30 and extends downwardly therefrom for guiding withdrawn samples of coal 2 into a storage bin for subsequent analysis.

A rectangular-shaped block 41, preferably formed of steel, is attached to top, bottom and side walls 26, 27 and 28, respectively, of a rearward extension 35 of probe 25 by welds 42 (FIGS. 2 and 3). A pneumatic vibrator 43 is fastened to block 41 by fasteners 44, and includes a port 39 which provides for pneumatic connection of the vibrator through tubing 40 to a usual pressurized air supply and controls therefore, of a type which is well-known in the art. Vibrator 43 preferably is a 2-inch piston pneumatic rapper type vibrator and provides for vibrating probe 25 to assist in the penetration of coal 2 by the probe, as well as to assist in the movement of a coal sample through the probe.

A pair of horizontal brackets 45 and 46 are mounted on top and bottom walls 26 and 27 of probe 25 by welds 47 (FIGS. 2 and 3). A pair of C-channel support bars 48 are attached at their front ends to brackets 45 and 46 and probe 25 by welds 49, at their intermediate portions to block 41 by welds 55, and at their rear ends to a crossplate 50 by welds 51 (FIG. 7). C-channel bars 48 stabilize, support and provide a means of attachment for probe 25 within housing 6.

An intermediate crossplate 52 and yoke 53 are positioned rearwardly of and adjacent to each other and to crossplate 50, with all three members 50, 52 and 53 being securely attached to each other by fasteners 54 and welds 56 (FIGS. 2, 3 and 7). A pair of ball bearing rollers 60 are mounted on the upper portion of yoke 53 by fasteners 61, with each roller 60 being positioned in contact with top wall 7 and adjacent to a respective one of side walls 9 of housing 6. Another pair of ball bearing rollers 62 are mounted on the lower portion of yoke 53 by usual fasteners. Each of the pair of rollers 62 has a flange 63 formed thereon for engaging a respective one of a pair of spaced tracks 64 formed on bottom wall 8 of housing 6. Thus, it can be seen that rollers 60 and 62 cooperate to prevent vertical movement of probe 25 within housing 6, and flanged rollers 62 additionally prevent sideward movement of the probe within the housing.

The front end of a square-shaped tube 72 extends through a complementary sized and shaped opening 71 formed in housing clamp 16 and is attached to the clamp by welds 73 (FIG. 4). Tube 72 is attached at its rear end to a pair vertically spaced angle brackets 74 by welds 75 and 68 (FIGS. 2 and 4). Each angle bracket 74, in turn, is attached to a front roller support and seal assembly closure 76 by a plurality of fasteners 69. A pair of rollers 78 are journaled in the upper portion of roller support 76 by shaft 77, and a similar pair of rollers 79 are journaled in the lower portion of roller support 76 by shaft 80. A flange 81, preferably formed of an abrasion-resistant ultra-high molecular weight (UHMW) polyethylene ring, is secured on each roller 78 by a retaining ring 82 seated in a groove. Upper rollers 78 engage top wall 26 of probe 25 and plastic flanges 81 engage side walls 28 of the probe. Similarly, a UHMW polyethylene ring is secured on each roller 79 by a retaining ring 84 seated in a groove. Lower rollers 79 engage bottom wall 27 of probe 25, and plastic flanges 83 engage side walls 28 of the probe. Formation of roller flanges 81 and 83 of an UHMW plastic reduces friction and wear between probe side walls 28 and the flanges. Thus, it can be seen that rollers 78 and 79 assist in preventing vertical and sideward movement of probe 25 for guiding and stabilizing the probe.

Figure 5:
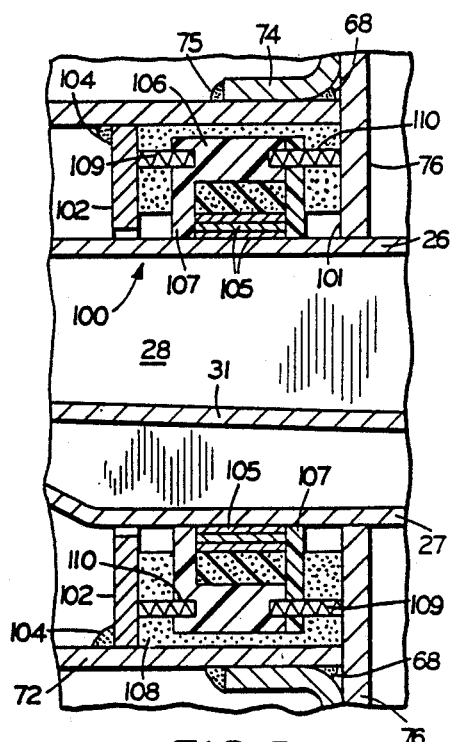
FIG. 5 is a greatly enlarged fragmentary sectional side view of an improved seal assembly for sealing the probe to the front end of the housing.
Figure 6:
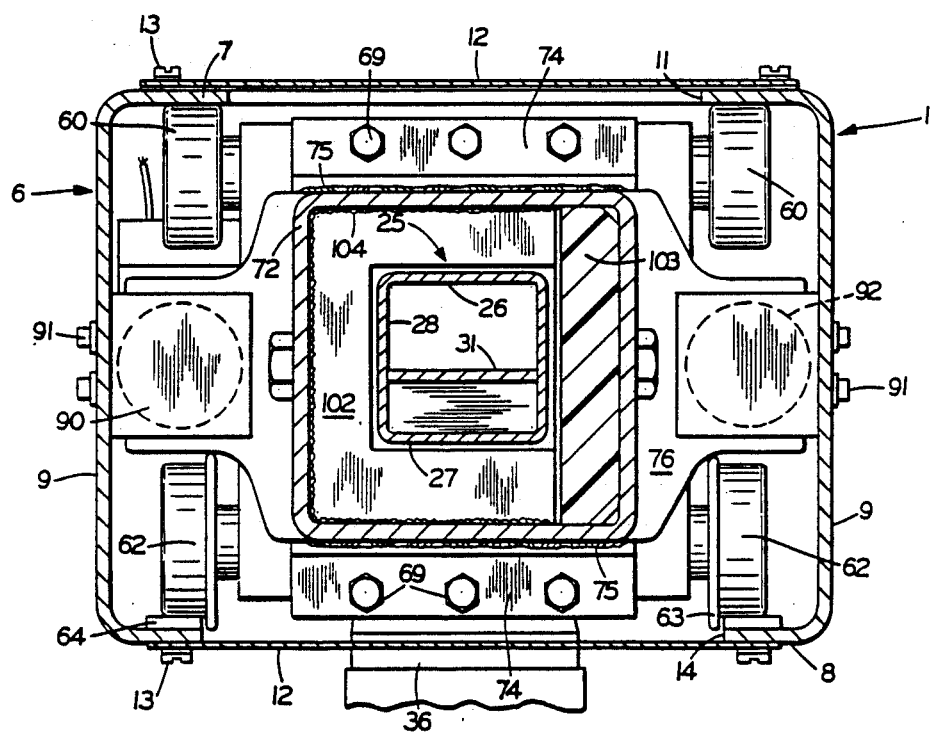
FIG. 6 is a sectional view taken on line 6—6, FIG. 4.

In accordance with another important feature of the invention, probe 25 is sealed to housing 6 by a seal assembly indicated generally at 100 (FIG. 5). Seal assembly 100 is housed in a compartment 101 defined by the rearward end of tube 72, seal assembly closure 76, and a generally U-shaped member 102 and a seal cavity 103 which are attached to tube 72 in a frontward spaced relationship to closure 76. U-shaped member 102 preferably is formed of metal and is attached to tube 72 by welds 104, and seal cavity 103 preferably is formed of UHMW polyethylene and is attached to tube 72 by any suitable means. Seal assembly 100 includes a plurality of compressed layers of contact members 105 which abut probe 25, which preferably are formed of an UHMW polyethylene felt, such as manufactured by Allied Signal Incorporated, High Performance Fibers Division, Petersburg, Va. and identified by the term Spectra 1000. If desired, this Spectra 1000 felt can be modified by impregnating it with a fluoropolymer suspension of the type identified as TFE-30 and manufactured by E.I. DuPont De Nemours & Co., Inc, of Wilmington, Del.

Compensation for wear to contact members 105 is provided by a resilient or springy member 106 positioned outwardly of and in abutment with the contact members (FIG. 5). Springy member 106 preferably is formed of closed-cell EPT sponge. A two-piece shell 107, preferably formed of abrasion-resistant UHMW polyethylene polymer, encases contact members 105 and springy members 106. To minimize transfer of vibrational energy from probe 25 to the other components of sampling apparatus 1 such as housing 6, a resilient member 108 is inserted between shell 107 and tube 72, seal assembly closure 76, U-shaped member 102, and seal cavity 103. Resilient member 108 preferably is formed of closed-cell EPT sponge. In addition, a pair of usual springs 109 are inserted in cavities 110 formed in shell 107 and resilient member 108.

Thus, seal assembly 100 effectively prevents coal 2 contained within pipe 3 from entering the rearward portions of housing 6 and interfering with the operation of the components contained therein, such as rollers 60, 62, 78, and 79. This is accomplished without diverting substantial amounts of the vibrational energy imparted to probe 25 by vibrator 43, and without interfering with the movement of the probe into and out of pipe 3. Thus, this vibrational energy will be directed to its intended use, that is, promotion of penetration of probe 25 into coal 2 moving through pipe 3, and transport of the sampled coal through the probe and out of probe outlet opening 30. In addition, the components of seal assembly 100 and their arrangement promote longer life of the seal assembly.

A pair of pneumatic cylinders 90 are mounted on housing side walls 9 by fasteners 91 (FIG. 2). Each cylinder includes a barrel 92 and a piston rod 93, with rod 93 extending rearwardly from the barrel through an adjustment clamping collar 94 and an opening 89 formed in crossplate 52, and is attached to a vibration isolation spring 95 by an adjustable threaded clamping collar 96. A pair of air ports 97 are formed in each cylinder barrel 92 providing for pneumatic connection of cylinders 90 to a usual pressurized air supply and controls (not shown). A pair of usual limit sensors 98 and 99, of a type well-known in the art, are positioned in spaced relationship on a selected one of cylinders 90 and are electrically connected to external controls by electrical connectors 88 for detecting the position of the probe.

A pneumatic cylinder 115 is mounted on a selected one of the housing sidewalls 9 and includes a barrel 116 and a piston rod 117 which extends through side wall 9 and into housing 6 (FIG. 8). A gate 118 is attached to the end of piston rod 117 by welds 113 and passes through tube 72, a seal assembly 114 inserted in seal cavity 103 and the seal cavity. Seal assembly 114 comprises a pair of contact members 120, preferably formed of UHMW polyethylene felt, which abut gate 118, and a pair of resilient members 121, preferably formed of closed-cell EPT sponge, which are positioned outwardly of and in abutment with contact members 120. A limit sensor 119 of a type which is well-known in the art is mounted on cylinder 115 and is electrically connected to control means by an electrical connector 122 for detecting the position of gate 118. More specifically, gate 118 is movable between open and closed positions and provides for closing open front end 24 of probe 25 when the probe is in the retracted position to prevent movement of coal 2 from pipe 3 into the probe between sampling cycles.

Figure 9:
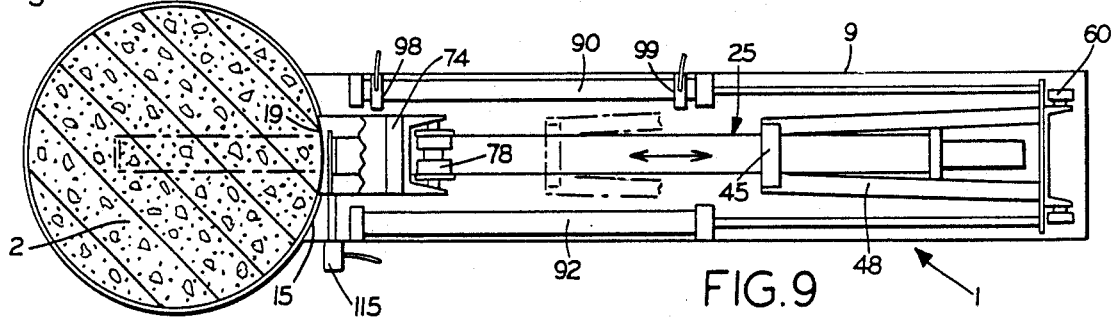
FIG. 9 is a schematic top view of the sampling apparatus of the present invention, shown mounted on a pipe having a granular material moving therethrough.
Figure 10:
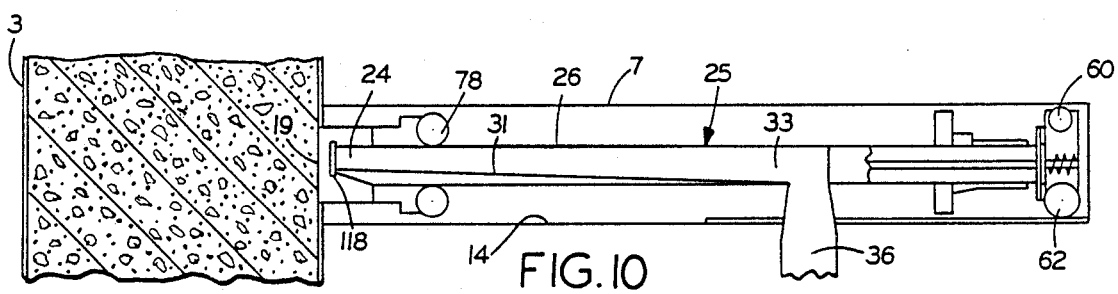
FIG. 10 is a schematic side view of the sampler, with its probe in the fully retracted position and the gate closing the open front end of the probe.

The operation of the improved sampling apparatus 1 of the present invention is set forth below. When sampler 1 is at-rest between sampling cycles, probe 25 is in the fully retracted position within housing 6 and gate 118 is in the closed position as shown in FIGS. 9 and 10. A sampling cycle is initiated at fixed time intervals or in response to a signal or signals indicating that a predetermined amount of granular material has moved through pipe 3. When a sampling cycle is initiated, gate 118 is moved to the open position by cylinder 115. When the gate reaches the fully open position, limit sensor 119 is activated. Activation of limit sensor 119 causes pneumatic cylinders 90 to become actuated which in turn causes pneumatic vibrator 43 to become actuated. Thus, pneumatic cylinders 90 move the vibrating probe into the pipe. Elongated slot 14 of housing 6 provides clearance for chute 36 as the probe moves between its retracted position within the housing and its extended position within the pipe.

Figure 11:
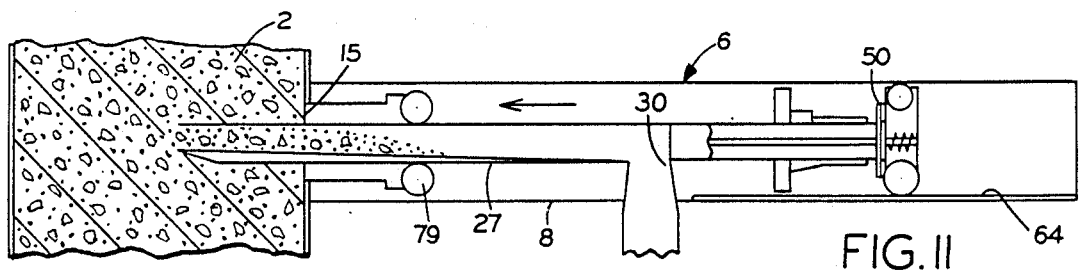
FIG. 11 is a schematic view similar to FIG. 10, showing the probe starting to extend into the pipe and granular material from the pipe entering the probe.

As the probe begins to enter the pipe as shown in FIG. 11, a sample of coal begins to move rearwardly through the probe under the influence of the vibrational forces applied to the probe and also by gravity due to sloping interior wall 31. It is important to note that the air pressure used to operate pneumatic cylinders 90 is regulated by the control means so that the forces applied by cylinders 90 to the probe are limited primarily to overcoming friction, thus allowing samples of the coal to move through the probe at a natural rate. This regulation avoids the problem of the probe being forced into the moving coal without coal entering the open front end 24 thereof at the same rate as the penetration rate of the probe. The regulation by the control means also ensures that all portions of the coal encountered by the probe tip are uniformly sampled. As a safety measure, if sensor 119 is not actuated within a specified time period, the control means for the sampling apparatus proceeds as though the gate is closed so that the sampling cycle is aborted and the user is warned.

Figure 12:
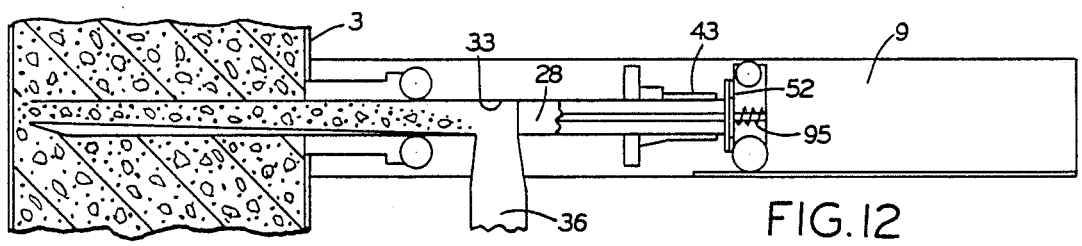
FIG. 12 is a schematic view similar to FIGS. 10 and 11, showing the probe fully extended into the pipe and the sample material moving toward the rear end of the probe.
Figure 13:
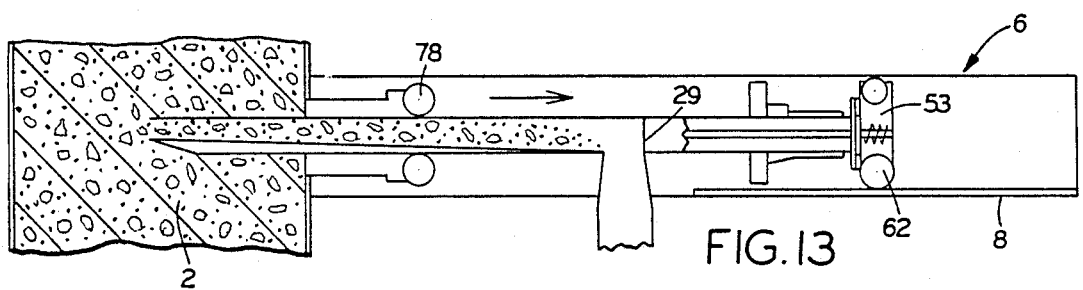
FIG. 13 is a schematic view similar to FIGS. 10-12, showing the sample-filled probe being retracted from the pipe.
Figure 14:
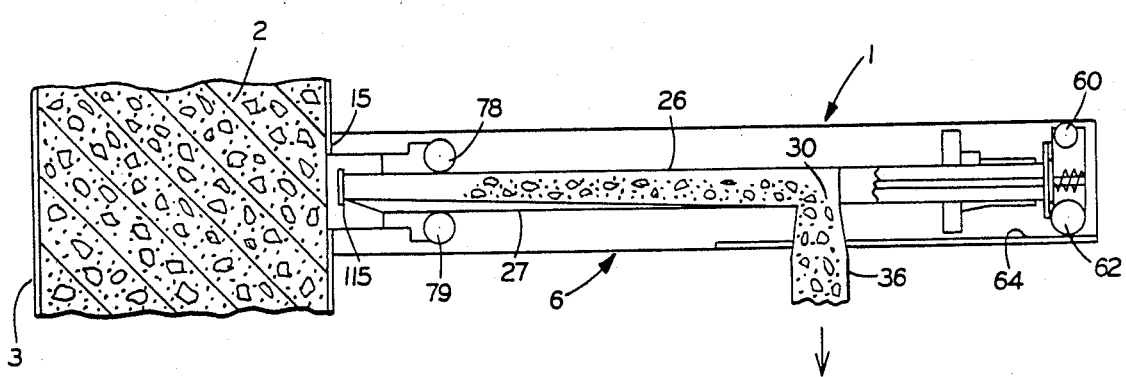
FIG. 14 is a schematic view similar to FIGS. 10-13, showing the probe in the fully retracted and closed position, and the sample moving through and out of the probe.

When the probe reaches its fully extended position within the pipe as illustrated in FIG. 12, the probe extends across nearly the entire width or diameter of the pipe so that a statistically unbiased sample is collected. Limit sensor 98 then is activated by the fully extended probe, or after a preset time, whichever occurs first, vibrator 43 is turned off and cylinders 90 retract the sample-filled probe from the pipe as shown in FIG. 13. As a safety measure, if for some reason the probe encounters an obstacle and cannot penetrate fully, retraction is provided for after a fixed time period so that movement of coal through the pipe is not blocked by the probe. A warning signal is sent to the user should such a condition arise. Limit sensor 99 then is activated when the probe is fully retracted as shown in FIG. 14, and in turn actuates cylinder 115 to automatically move gate 118 to the closed position. The probe then remains in the retracted position until the next sampling cycle.

After closure of gate 118, vibrator 43 again is automatically actuated by the control means and applies vibration to the retracted probe for a fixed period of time. The vibration of the probe clears the probe by moving any sample residue remaining therein through the probe, out of outlet opening 30 and into chute 36 leading to a suitable storage container via a preferably flexible pipe 85 (FIG. 3) for subsequent sampling, as illustrated in FIG. 14. When the gate is in the closed position, a small clearance is maintained between the gate and cutter tips 34 of the retracted probe. This clearance prevents damage to the gate or tips during the vibratory residue-clearing step. This last vibration step can be eliminated where samples from multiple sample cycles are being combined to form a single gross sample. Thus, residual amounts of sample are stored in the probe after each sample cycle and are displaced by a new sample from the next cycle. However, after collection of a single sample or at the conclusion of collecting multiple samples for a single gross sample, the above vibratory residue-clearing step is initiated prior to the next sample cycle.

It is to be understood that means other than pneumatic cylinders 90 and 115, and pneumatic vibrator 43, can be used to move the probe and gate, and to vibrate the probe, respectively, without effecting the concept of the invention. Such other means could include an electromagnetic vibrator or a motor for vibrating the probe, and hydraulic cylinders or motors for moving the probe and gate.

Figure 15:
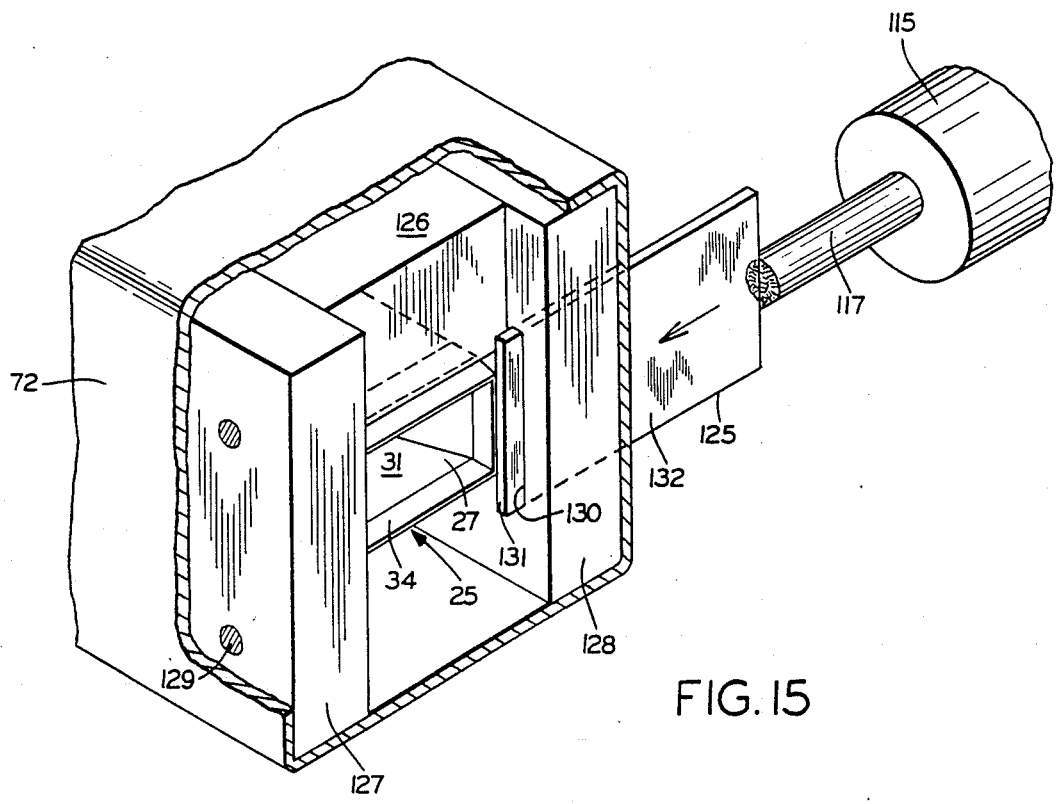
FIG. 15 is a fragmentary perspective view, with portions broken away and in section, of a second embodiment of the gate for closing the open front end of the probe.

A second embodiment of the gate for closing the open front end of the probe is indicated at 125 and shown in FIG. 15, and is similar to gate 118 of the first embodiment except for the manner in which closure of open front end 24 of probe 25 is achieved. As discussed above, a small clearance is maintained between gate 118 and cutter tips 34 of probe 25 when the probe is retracted and the gate is closed to prevent damage to the gate or probe tips during the vibratory residue-clearing step. However, it is possible that residue from the material being sampled could enter the probe channel between sample cycles through the clearance area between gate 118 and the cutter tips.

Thus, the second embodiment of the gate for closing the probe is desirable in certain applications, where it is necessary to substantially reduce the possibility that residue of the material being sampled will enter the probe channel. More particularly, although clearance is maintained between gate 125 and cutter tips 34, gate 125 will be closed along three of its edges. More particularly, a plurality of blocks 126, 127 and 128, all preferably formed of UHMW polyethylene, are mounted on the top and sidewalls of square tube 72 by usual fasteners 129. Gate 125 passes through a slot 130 formed in block 128 and a seal assembly (not shown) which is embedded in the block and which is similar to seal assembly 114 of the first embodiment for sealing gate 125 to block 128. As gate 125 moves toward the closed position, its rear surface is in contact with block 126. When gate 125 reaches the fully closed position, side edge 131 of the gate abuts block 127. Although clearance remains between bottom edge 132 of gate 125 and cutter tip 34 of bottom wall 27 of the probe, gravity and friction will substantially prevent residue of the material being sampled from entering the probe. It should be noted that blocks 126–128 also will aid in retaining seal assembly 100 in place.

Again, one of the important features of sampling apparatus 1 is seal assembly 100 which seals probe 25 to housing 6 without appreciably interfering with the movement of the probe into and out of the pipe carrying the material to be sampled. Seal assembly 100 also does not substantially divert the vibrational forces applied to the probe to other parts of the sampling apparatus. Another important feature is the diverging taper of the interior channel of the probe which ensures that the sample obtained by the probe will not jam the probe.

In addition, vibrator 43 which applies vibration to the probe for aiding in penetration of the probe into the material moving through the pipe and for assisting in moving the sample through the probe, is another important feature of the invention. Also important are the cylinders for moving the probe into and out of the pipe and for opening and closing the gate, along with the limit sensors which detect the position of the probe and gate for initiating various steps in the sampling cycle.

Accordingly, the improved sampler of the invention for sampling granular material moving through a pipe is simplified, provides an effective, safe, inexpensive, and efficient apparatus which achieves all the enumerated objectives, provides for eliminating difficulties encountered with prior sampling apparatus, and solves problems and obtains new results in the art.

In the foregoing description, certain terms have been used for brevity, clearness and understanding; but no unnecessary limitations are to be implied therefrom beyond the requirements of the prior art, because such terms are used for descriptive purposes and are intended to be broadly construed.

Moreover, the description and illustration of the invention is by way of example, and the scope of the invention is not limited to the exact details shown or described.

Having now described the features, discoveries and principles of the invention, the manner in which the sampler for granular material moving through a pipe is constructed and used, the characteristics of the improved apparatus, and the advantageous, new and useful results obtained; the new and useful structures, devices, elements, arrangements, parts, and combinations, are set forth in the appended claims.

I claim:

1. An apparatus for sampling a granular material moving through a pipe, said apparatus including:
    (a) a housing having an open front end, said housing being mounted on the pipe so that said open front end is aligned with an opening formed in the pipe;
    (b) a hollow probe having an open front end, said probe being movably mounted within the housing for removing a sample of the granular material from the pipe;
    (c) means for selectively moving the probe between position within the housing and through the open front end of said housing to an extended position within the pipe;
    (d) means for selectively vibrating the probe to assist the probe in penetrating the granular material within the pipe to obtain a sample of said granular material within said probe and for moving the sample through the probe;
    (e) means for sealing the probe to the front end of the housing; and (f) means for selectively closing the probe at a selected point along the probe to prevent movement of the granular material through the probe upon the probe moving toward a retracted position.

2. The apparatus defined in claim 1 in which the open front end of the housing has a contour generally complementary to the contour of the pipe for snugly mounting the housing on the pipe.

3. The apparatus defined in claim 1 in which a circular clamp is attached to the open front end of the housing for removably mounting the housing on and perpendicular to the pipe.

4. The apparatus defined in claim 1 in which the hollow probe includes an interior wall which slopes downwardly rearwardly away from the open front end of the probe to form a rearwardly divergent channel within the probe providing for movement of a sample of the granular material through the probe by gravity; and in which the front end of the probe terminates in beveled cutter tips providing for penetration of the granular material moving through the pipe by the probe.

5. The apparatus defined in claim 1 in which the housing is elongated and generally rectangular-shaped and includes top, bottom, side, and rear walls; and in which an elongated, longitudinally extending slot is formed in the bottom wall.

6. The apparatus defined in claim 5 in which the probe is an elongated, generally rectangular-shaped member having top, bottom, side and rear walls; in which a front end of the bottom wall is beveled upwardly; in which an outlet opening is formed in the bottom wall of the probe adjacent to the rear wall thereof; in which a chute extends downwardly from the bottom wall of the probe and is aligned with the outlet opening; and in which the chute is positioned to traverse the elongated slot formed in the bottom wall of the housing when the probe moves between its retracted position within the housing and its extended position within the pipe.

7. The apparatus defined in claim 1 in which the means for selectively moving the probe is a pair of pneumatic cylinders mounted within the housing and operatively connected to the probe; and in which a pair of limit sensors are mounted on one of the pneumatic cylinders and are electrically connected to control means for detecting the moving probe for controlling the pneumatic cylinders and the means for vibrating and closing the probe.

8. The apparatus defined in claim 1 in which the means for selectively vibrating the probe is a pneumatic vibrator mounted on the probe.

9. The apparatus defined in claim 1 in which a plurality of rollers are mounted within the housing for stabilizing and guiding the moving probe within said housing.

10. The apparatus defined in claim 1 in which the means for sealing the probe to the front end of the housing is a plurality of resilient and abrasion resistant materials mounted within a compartment formed adjacent to the front end of the housing.

11. The apparatus defined in claim 10 in which the plurality of resilient and abrasion resistant materials includes contact means for abutting the probe, resilient force means positioned outwardly of and abutting the contact means for compensating for wear to the contact means, shell means for encasing the contact and resilient force means, and resilient means inserted outwardly of and adjacent to the shell means for minimizing transfer of vibrational energy from the probe to other components of the sampling apparatus, and spring means inserted in cavities formed in the shell means and resilient means for further minimizing transfer of vibrational energy from the probe to other components of the sampling apparatus.

12. The apparatus defined in claim 1 in which the means for closing the probe is a gate movably mounted adjacent to the front end of the housing for substantially closing the open front end of the probe when the probe is in the retracted position; in which the gate is operatively connected to a pneumatic cylinder mounted on the housing; and in which a limit sensor is mounted on the pneumatic cylinder and is electrically connected to control means for detecting the moving gate for controlling the operation of the means for moving and vibrating the probe.

13. The apparatus defined in claim 1 in which the means for closing the probe is a gate movably mounted adjacent to the front end of the housing; in which the gate is operatively connected to a pneumatic cylinder mounted on the housing for moving said gate between open and closed positions; in which a limit sensor is mounted on the pneumatic cylinder and is electrically connected to control means for detecting the moving gate for controlling the means for moving and vibrating the probe; and in which the gate is spaced from the open front end of the probe and abuts at least one closure member which extends frontwardly of said open front end for substantially closing the probe when the probe is in the retracted position and the gate is in the closed position.

14. An improved apparatus for sampling a granular material moving through a pipe, including:
(a) a housing having an open front end, said housing being mounted on the pipe so that said open front end is aligned with an opening formed in the pipe;
(b) a hollow probe having an open front end, said being movably mounted within the housing for removing a sample of the granular material from the pipe;
(c) means for selectively moving the probe between a retracted position within the housing and through the open front end of said housing to an extended position within the pipe;
(d) means for selectively vibrating the probe to assist the probe in penetrating the granular material within the pipe to obtain a sample of said granular material within said probe and for moving the sample through the probe;
(e) means for selectively closing the probe at a selected point along the probe to prevent movement of the granular material through the probe;
(f) contact means for surrounding and abutting the probe;
(g) resilient force means positioned outwardly of and surrounding and abutting the contact means for compensating for wear to the contact means;
(h) shell means for encasing the contact and resilient force means; and
(i) resilient means inserted between the shell means and a compartment adapted to retain the contact, resilient force, shell, and resilient means adjacent to the front end of the housing.

15. The apparatus defined in claim 14 in which the contact means is formed of ultrahigh molecular weight polyethylene felt.

16. The apparatus defined in claim 14 in which the contact means is formed of fluoropolymer impregnated ultrahigh molecular weight polyethylene felt.

17. The apparatus defined in claim 14 in which the resilient force means is a generally square-shaped ring member formed of closed-cell EPT sponge.

18. The apparatus defined in claim 14 in which the shell means is a two-piece generally square-shaped ring member formed of abrasion-resistant UHMW polyethylene and having an inwardly-facing channel formed therein.

19. The apparatus defined in claim 18 in which the resilient means is a generally square-shaped ring member formed of closed-cell EPT sponge and having an inwardly-facing channel formed therein, and at least one spring inserted in cavities formed in the resilient means and shell means.

20. An apparatus for sampling a granular material, including:
 (a) a housing having an open front end;
 (b) a probe movably mounted within the housing for obtaining a sample of the granular material, said probe having an open front end and a rearwardly divergent channel formed therein providing for movement of a sample of the granular material through the probe;
 (c) means for selectively moving the probe between a retracted position within the housing and through the open front end of said housing to an extended position and into the granular material;
 (d) means for selectively vibrating the probe to assist the probe in penetrating the granular material for obtaining a sample of the granular material within the probe and for moving the sample through the probe; and
 (e) means for selectively closing the probe channel at a selected point along the probe.

21. The apparatus described in claim 20 in which a plurality of resilient and abrasion resistant materials seal the probe to the front end of the housing.

22. An apparatus for closing a sampler probe of the type having an open front end, said apparatus including:
 (a) a plate;
 (b) a pneumatic piston for moving the plate between open and closed positions with said plate being spaced from the open front end of the probe when in the closed position, said piston comprising a rod and a barrel with the plate being attached to the rod;
 (c) a top and a pair of side contact members extending frontwardly of the open front end of the probe, for abutting the plate when said plate passes through a slot formed in a selected one of the side contact members and is moved to the closed position to substantially close the open front end of the probe; and
 (d) seal means embedded in the selected side contact member adjacent to the slot, for sealing the plate to said selected side member.

23. An apparatus for closing a sampler probe of the type having an open front end, said apparatus including:
 (a) a plate;
 (b) a piston for linearly moving the plate between an open position and a closed position, with said plate being spaced from the open front end of the probe when in the closed position; and
 (c) at least one separate contact member extending frontwardly of the open front end of the probe for abutting the plate when said plate is in the closed position to substantially close the open front end of the probe.

24. The apparatus defined in claim 23 in which a top and a pair of side contact members extend frontwardly of the open front end of the probe and abut the plate when said plate is in the closed position.

25. The apparatus defined in claim 24 in which a slot is formed in a selected one of the contact members; in which the plate passes through the slot when said plate is moved to the closed position; and in which seal means is embedded in the selected contact member adjacent to the slot for sealing the plate to said selected member.

26. The apparatus defined in claim 23 in which the piston is a pneumatic piston having a rod and a barrel; and in which the plate is attached to the rod.

* * * * *